US012590097B2

(12) United States Patent
Zhong et al.

(10) Patent No.: US 12,590,097 B2
(45) Date of Patent: Mar. 31, 2026

(54) SUBSTITUTED ENTECAVIR MONOPHOSPHATE ALANINAMIDE PHENOLIC ESTERS FOR RESISTING HEPATITIS B VIRUS

(71) Applicant: BEIJING JUNKE HUAYUAN MED TECH CO., LTD., Beijing (CN)

(72) Inventors: Bohua Zhong, Beijing (CN); Hongwu Li, Beijing (CN); Xiaozai Wang, Beijing (CN)

(73) Assignee: BEIJING JUNKE HUAYUAN MED TECH CO., LTD., Beijing (CN)

( * ) Notice: Subject to any disclaimer, the term of this patent is extended or adjusted under 35 U.S.C. 154(b) by 716 days.

(21) Appl. No.: 17/907,684

(22) PCT Filed: Apr. 1, 2021

(86) PCT No.: PCT/CN2021/084958

§ 371 (c)(1),
(2) Date: Sep. 29, 2022

(87) PCT Pub. No.: WO2021/204059

PCT Pub. Date: Oct. 14, 2021

(65) Prior Publication Data

US 2023/0130464 A1 Apr. 27, 2023

(30) Foreign Application Priority Data

Apr. 8, 2020 (CN) ......................... 202010273139.9

(51) Int. Cl.

| | |
|---|---|
| ***A61K 31/522*** | (2006.01) |
| ***A61K 9/00*** | (2006.01) |
| ***A61K 9/20*** | (2006.01) |
| ***C07D 487/04*** | (2006.01) |

(52) U.S. Cl.

CPC .......... *C07D 487/04* (2013.01); *A61K 9/0056* (2013.01); *A61K 9/20* (2013.01)

(58) Field of Classification Search

CPC ............................ A61K 31/522; C07D 487/04
USPC ........................................ 514/263.4; 544/276
See application file for complete search history.

(56) References Cited

FOREIGN PATENT DOCUMENTS

| | | | |
|---|---|---|---|
| CN | 103804417 | A | 5/2014 |
| CN | 104151360 | A | 11/2014 |
| CN | 109689065 | A | 4/2019 |
| WO | 2015077360 | A2 | 5/2015 |
| WO | 2018022221 | A1 | 2/2018 |

OTHER PUBLICATIONS

Ross, Bruce S. et al.; "Synthesis of Diastereomerically Pure Nucleotide Phosphoramidates": The Journal of Organic Chemistry: Sep. 14, 2011; vol. 76; pp. 8311-8319.

*Primary Examiner* — Douglas M Willis
(74) *Attorney, Agent, or Firm* — NKL Law; Allen Xue

(57) ABSTRACT

An entecavir monophosphate alaninamide phenolic ester derivative is represented by formula II. It has non-toxic pharmaceutically acceptable salts. In formula II, X is H, halogen, R or —OR, and R is a $C_{1-3}$ alkyl or a substituted $C_{1-3}$ alkyl. The entecavir monophosphate alaninamide phenolic ester derivative or the non-toxic pharmaceutically acceptable salt thereof can be used in the preparation of a drug for resisting the hepatitis B virus.

(II)

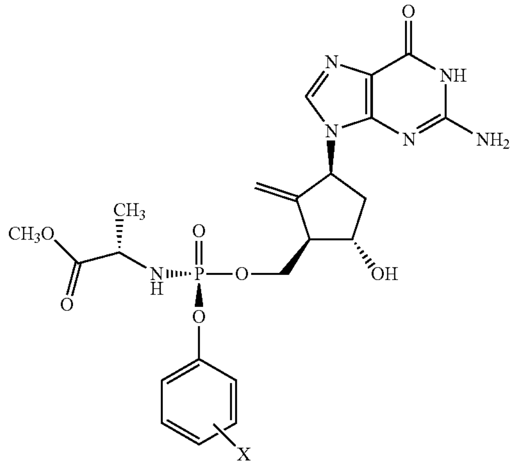

11 Claims, No Drawings

SUBSTITUTED ENTECAVIR MONOPHOSPHATE ALANINAMIDE PHENOLIC ESTERS FOR RESISTING HEPATITIS B VIRUS

This application is a U.S. national stage entry of PCT International Application No. PCT/CN2021/084958, filed on Apr. 1, 2021, which claims the priority to Chinese Patent Application No. 202010273139.9, filed with the China National Intellectual Property Administration on Apr. 8, 2020, and entitled "ENTECAVIR MONOPHOSPHATE ALANINAMIDE PHENOLIC ESTER AND MEDICAL USE THEREOF", the content of which is incorporated herein by reference in its entirety.

TECHNICAL FIELD

The present disclosure belongs to the field of medical technology, and specifically relates to a novel entecavir monophosphate alaninamide phenolic ester derivative and a non-toxic pharmaceutically acceptable salt thereof, and use thereof for the manufacturing of a medicament for resisting the hepatitis B virus.

BACKGROUND

Viral hepatitis is a major disease that threatens human health. Entecavir is currently the most effective therapeutic drug for hepatitis B. However, entecavir and lamivudine have certain cross resistance, and entecavir has a poor curative effect on lamivudine-resistant patients. In addition, similar to other nucleoside anti-HBV drugs, diseases treated by entecavir are prone to relapse after interruption. In addition, the results of experimental evaluation in animals show that entecavir has certain carcinogenicity.

As a nucleoside analog, entecavir is phosphorylated in vivo into entecavir monophosphate, which is further transformed into an active form of entecavir triphosphate to inhibit the replication of HBV and exert the anti-HBV effect.

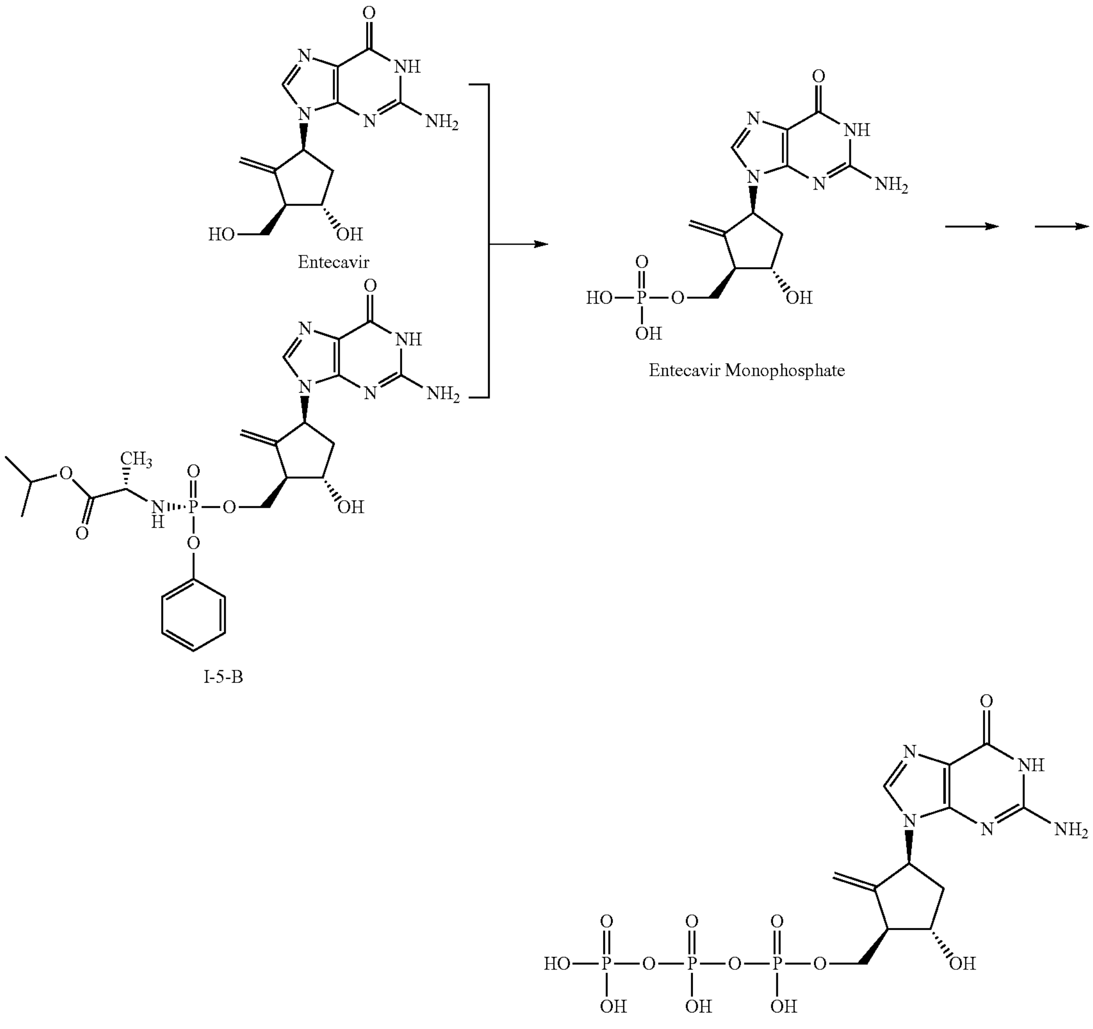

Entecavir

I-5-B

Entecavir Monophosphate

Entecavir Triphosphate

The Chinese Patent Application for Invention CN103804417A disclosed a series of entecavir phosphamide/phenolic ester derivatives, and the compound I-5-B (Example 7) with the best activity was found to have a good antiviral effect on hepatitis B in vivo in ducks. The compound I-5-B is subjected to enzymolysis in vivo to generate entecavir monophosphate, which is further transformed into entecavir triphosphate.

However, the inventors have found in subsequent development and research that in beagle dogs, which have metabolic properties closer to those of humans, the I-5-B can not be completely transformed into the active form, and that a high concentration of the prodrug prototype is present in plasma, which may cause unpredictable toxicity or side effects.

SUMMARY

The present disclosure provides an entecavir monophosphate alaninamide phenolic ester derivative of formula II or a non-toxic pharmaceutically acceptable salt thereof:

II

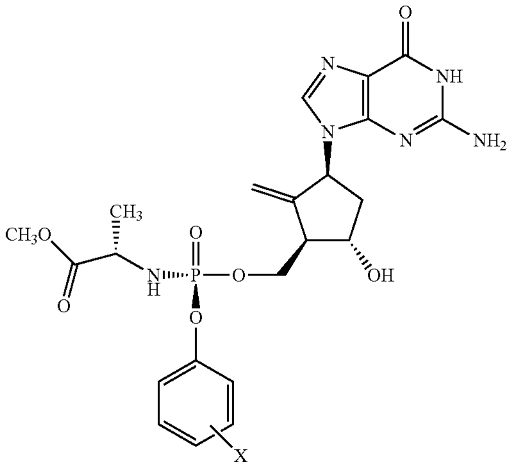

In the formula II, X is H, halogen, R or —OR, and R is $C_{1-3}$ alkyl or substituted $C_{1-3}$ alkyl.

In some embodiments, the substituted $C_{1-3}$ alkyl is $C_{1-3}$ alkyl substituted with hydroxyl or a halogen.

In some embodiments, the halogen is F, Cl, Br or I, preferably F, Cl or Br.

In some embodiments, R is a methyl, ethyl or propyl.

In some embodiments, X is H, F, Cl, Br, methyl or methoxy.

In some embodiments, X is located on the para-position carbon atom. For example, X is a para-position F, Cl, Br, methyl or methoxy.

In some embodiments, the entecavir monophosphate alaninamide phenolic ester derivative of formula II is selected from the compounds in the following table:

II-1

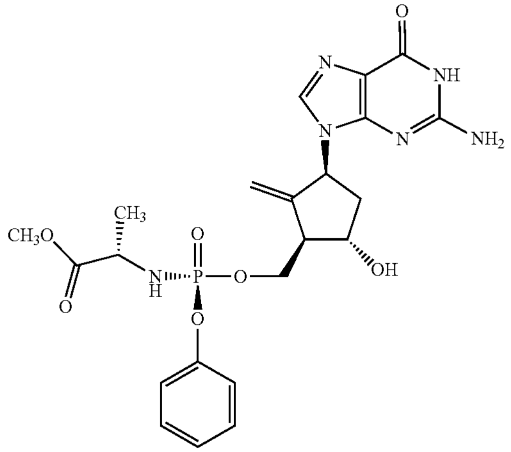

II-2

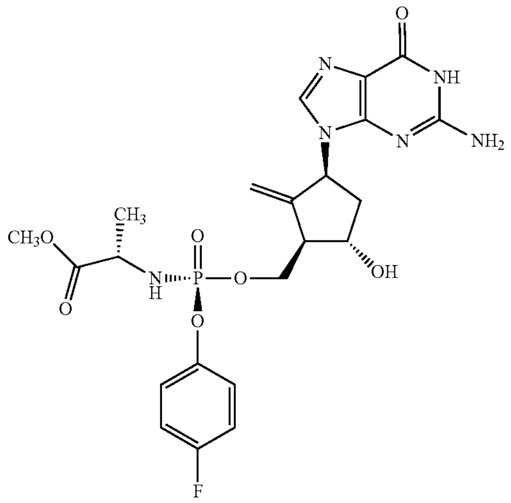

-continued

II-3

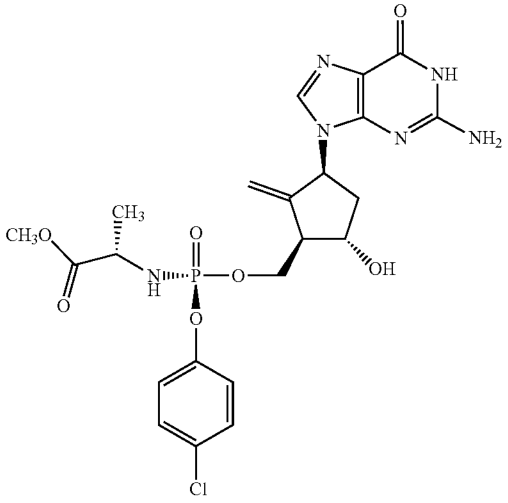

II-4

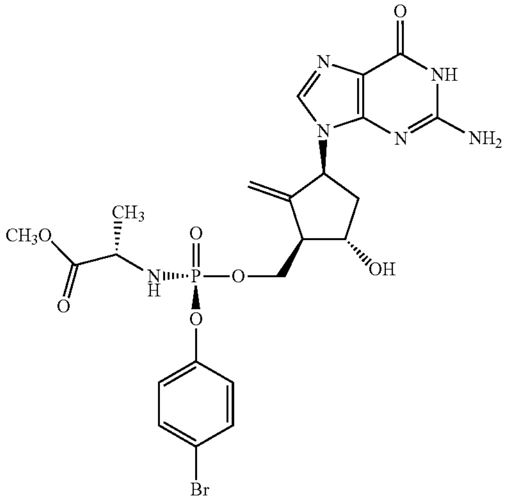

II-5

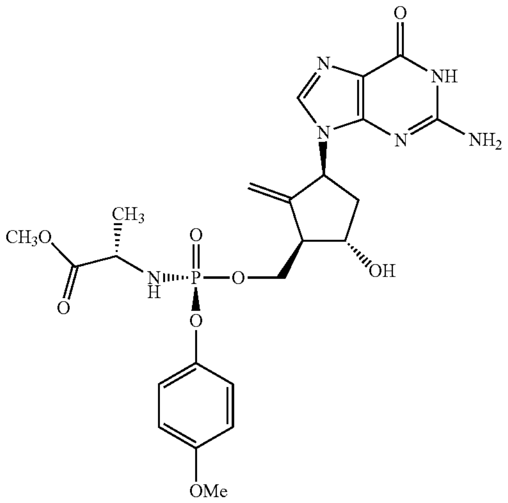

-continued

II-6

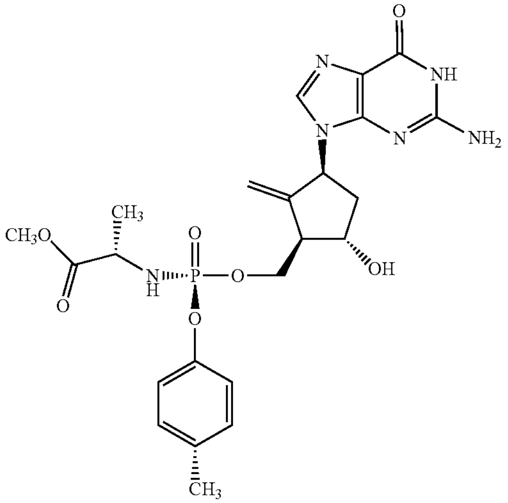

The present disclosure further provides a pharmaceutical composition comprising the entecavir monophosphate alaninamide phenolic ester derivative of formula II or the non-toxic pharmaceutically acceptable salt thereof described above as an active ingredient.

In some embodiments, the pharmaceutical composition is a capsule, a tablet, a granule, a powder, a suspension, a solution or a lozenge.

The present disclosure further provides use of the entecavir monophosphate alaninamide phenolic ester derivative of formula II or the non-toxic pharmaceutically acceptable salt thereof described above or the pharmaceutical composition comprising the entecavir monophosphate alaninamide phenolic ester derivative or the non-toxic pharmaceutically acceptable salt thereof described above as an active ingredient for the manufacturing of a medicament for resisting hepatitis B virus.

The present disclosure further provides a method for treating a disease caused by the hepatitis B virus, which comprises the following step: administering to a subject in need a therapeutically effective amount of the entecavir monophosphate alaninamide phenolic ester derivative of formula II or the non-toxic pharmaceutically acceptable salt thereof described above or the pharmaceutical composition comprising the entecavir monophosphate alaninamide phenolic ester derivative of formula II or the non-toxic pharmaceutically acceptable salt thereof described above as an active ingredient.

The present disclosure further provides use of the entecavir monophosphate alaninamide phenolic ester derivative of formula II or the non-toxic pharmaceutically acceptable salt thereof described above or the pharmaceutical composition comprising the entecavir monophosphate alaninamide phenolic ester derivative of formula II or the non-toxic pharmaceutically acceptable salt thereof described above as an active ingredient for treating diseases caused by hepatitis B virus infection.

According to the present disclosure, diseases caused by hepatitis B virus infection include acute hepatitis B and chronic hepatitis B.

DETAILED DESCRIPTION

The technical solutions of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared by known methods.

The compounds of the present disclosure can be prepared according to the following synthetic route:

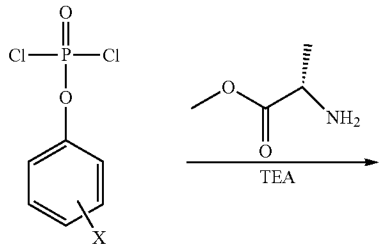

i

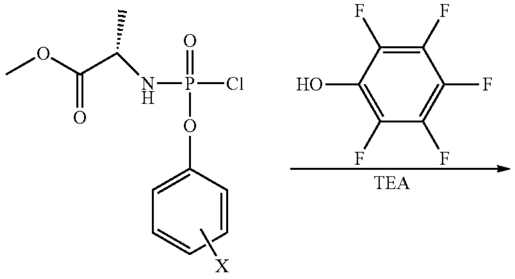

ii

-continued

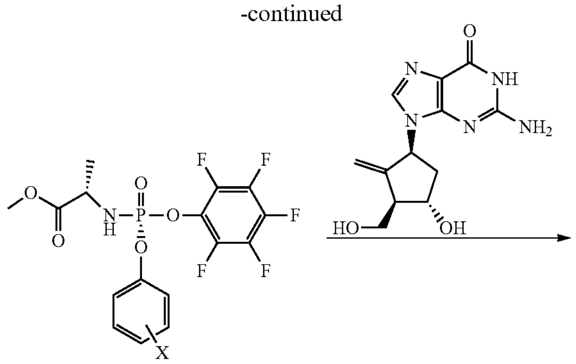

iii

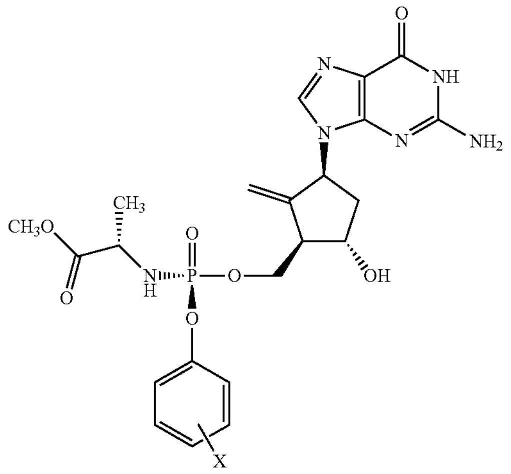

II

Referring to the method reported in the literature (Ross B S, et al., Synthesis of Diastereomerically Pure Nucleotide Phosphoramidates. *J Org Chem,* 2011, 76: 8311-8319), phenyl phosphorodichloridate (i) is used as a starting material to react with methyl alaninate to obtain a phosphamidophenolic ester intermediate (ii); the (ii) and pentafluorophenol are subjected to a condensation reaction to prepare a key chiral intermediate methyl (S)-2-[(S)-(2-pentafluorophenoxy)-phenoxy-phosphorylamino]propionate (iii); and the (iii) is reacted with entecavir to prepare the target compound II.

In the reaction formula, X is H, halogen, R or —OR, and R is $C_{1-3}$ alkyl or substituted $C_{1-3}$ alkyl, as defined in the Summary of the present disclosure.

Reference Example 1: Preparation of 2-amino-1,9-dihydro-9-[(1S,3R,4S)-4-hydroxy-3-((S)-((S)-1-isopropoxycarbonylethylamino-phe noxy-phosphoryl)-oxymethyl)-2-methylenecyclopentyl]-6H-purin-6-one (I-5-B)

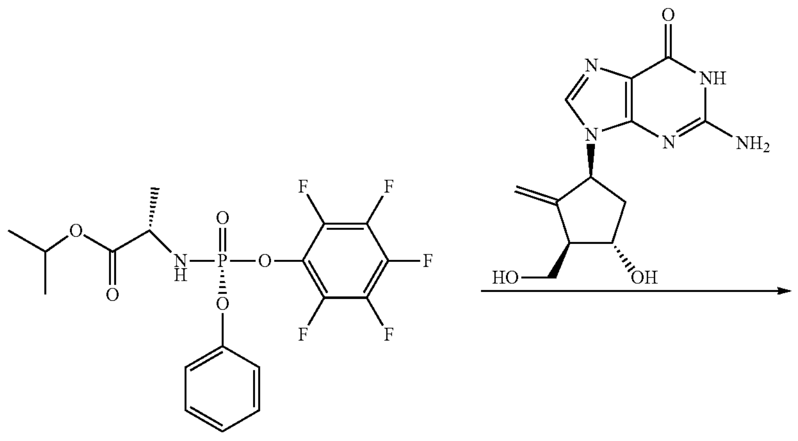

iii-0

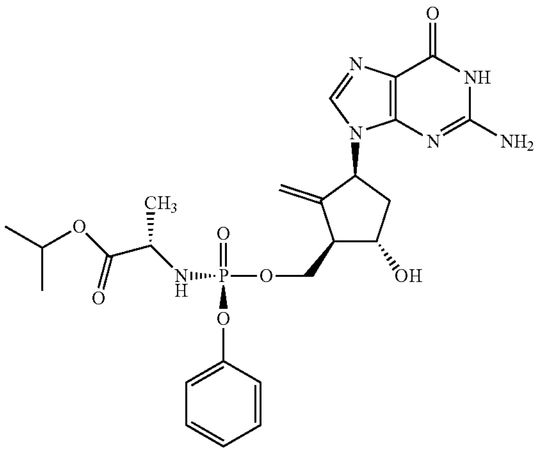

I-5-B 4 g of anhydrous entecavir was dissolved in 80 mL of DMF, and the reaction system was cooled to −5° C. and stirred for 10 min; then 40 mL of 0.47 mol/L tert-butyl magnesium bromide was added dropwise to the reaction system, and the resulting reaction system was stirred at −5° C. for 30 min. A solution of 7.8 μg of isopropyl (S)-2-[-(S)-(2,3,4,5,6-pentafluoro-phenoxy)-phenoxy-phosphoramide]-propionate (iii-0, the product of Suzhou Keyuan Pharmaceutical Technology Co., Ltd.) in 40 mL of THE was added dropwise to the reaction system; and after the addition was completed, the reaction system was slowly warmed to room temperature and mixed for 16 h. Then 200 mL of dichloromethane was added to the reaction liquid, and the mixture was placed in a separating funnel and washed with saturated brine (2×200 mL), and the organic layer was separated out. The organic layer was dried over anhydrous sodium sulfate overnight and filtered, and the filtrate was concentrated under reduced pressure, mixed with silica gel, loaded on a silica gel chromatography column, and eluted with a mixed solvent of dichloromethane, methanol and aqueous ammonia (10:1:0.1), and the desired components were collected, combined and evaporated to dryness under reduced pressure to obtain 0.7 g of I-5-B. δ (ppm, DMSO-$d_6$, 400 MHz) in $^1H$ NMR spectroscopy: 1.13-1.18 (6H, m), 1.24 (3H, d), 2.04-2.09 (1H, m), 2.26-2.33 (1H, m), 2.74 (1H, s, br), 3.79-3.84 (1H, m), 4.06-4.10 (1H, m), 4.21-4.27 (2H, m), 4.61 (1H, s, br), 4.84-4.92 (1H, m), 5.07 (1H, d), 5.16 (1H, s, br), 5.41 (1H, m), 6.03-6.08 (1H, m), 6.45 (2H, s, br), 7.16-7.24 (3H, m), 7.36-7.40 (2H, m), 7.66 (1H, s), 10.57 (1H, s, br).

Example 1: 2-amino-1,9-dihydro-9-[(1S,3R,4S)-4-hydroxy-3-((S)-((S)-1-methoxycarbonylethylamino-phenoxy-phosphoryl)-oxymethyl)-2-methylenecyclopentyl]-6H-purin-6-one (II-1)

II-1

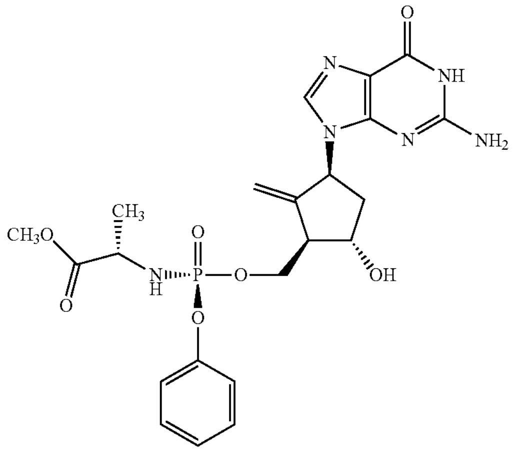

Step 1.1 Preparation of methyl (S)-2-[-(S)-(2,3,4,5,6-pentafluoro-phenoxy)-phenoxy-phosphoramide]-propionate (iii-1)

Referring to the method reported in the literature (Ross B S, et al., Synthesis of Diastereomerically Pure Nucleotide Phosphoramidates. *J Org Chem,* 2011, 76: 8311-8319.), 6.6 g of L-alanine methyl ester hydrochloride (0.047 mol) was dissolved in 50 mL of anhydrous dichloromethane, and the reaction system was cooled to −70° C., and 13.8 mL of triethylamine was added dropwise; then a solution of 10 g of phenyl dichlorophosphate in 40 mL of anhydrous dichloromethane was added dropwise to the reaction system. The reaction system was warmed to 0° C. over 2 h, and then stirred for 1 h. A solution of 8.7 g of pentafluorophenol and 7.3 mL of triethylamine in 30 mL of anhydrous dichloromethane was added to the reaction mixture over 20 min; and the reaction mixture was stirred at 0° C. for 4 h, the white solid was filtered off, and the filter cake was rinsed with 20 mL of dichloromethane. The filtrate was evaporated to dryness under reduced pressure, and the residue was recrystallized twice with a mixed solvent of n-hexane/ethyl acetate (4:1) to obtain 3.8 g of iii-1 as a white solid with a de value of 98.6%. δ(ppm, DMSO-$d_6$, 400 MHz) in $^1$H NMR spectroscopy: 1.28 (3H, d), 3.61 (3H, s), 3.96-4.06 (1H, m), 6.91-6.97 (1H, m), 7.23-7.28 (3H, m), 7.40-7.45 (2H, m).

Step 1.2 Preparation of Compound II-1 Referring to the method of Reference Example, the iii-1 was in place of isopropyl (S)-2-[-(S)-(2,3,4,5,6-pentafluoro-phenoxy)-phenoxy-phosphoramide]-propionate (iii-0) to react with anhydrous entecavir, and the reaction product was separated by silica gel column chromatography to obtain the compound II-1 with a yield of 15%. δ (ppm, DMSO-$d_6$, 400 MHz) in $^1$H NMR spectroscopy: 1.24 (3H, d), 2.04-2.09 (1H, m), 2.26-2.33 (1H, m), 2.75 (1H, s, br), 3.61 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.16-7.24 (3H, m), 7.36-7.40 (2H, m), 7.66 (1H, s), 10.55 (1H, s).

Example 2: 2-amino-1,9-dihydro-9-[(1S,3R,4S)-4-hydroxy-3-((S)-((S)-1-methoxycarbonylethylamino-(4-fluoro-phenyl)oxy-phosphoryl)-oxymethyl)-2-methylenecyclopentyl]-6H-purin-6-one (11-2)

II-2

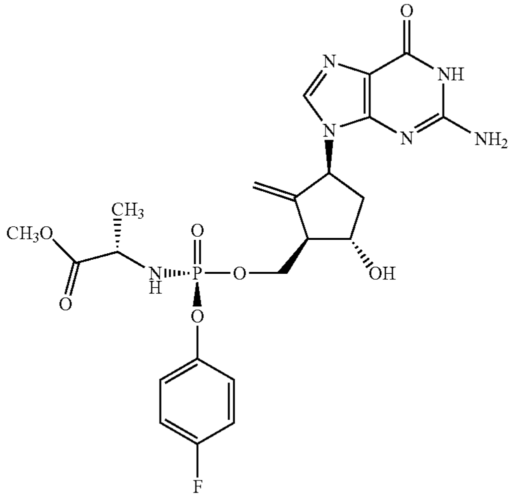

Referring to the method in step 1.1 of Example 1, dichlorophosphoric acid-(p-fluoro-phenol)ester was in place of dichlorophosphoric acid phenol ester to react with L-alanine methyl ester hydrochloride and pentafluorophenol successively, thus obtaining methyl (S)-2-[-(S)-(2,3,4,5,6-pentafluoro-phenoxy)-(p-fluorophenoxy)-phosphoramide]-propionate (iii-2) with a yield of 25% and a de value of 98.2%. δ (ppm, DMSO-$d_6$, 400 MHz) in $^1$H NMR spectroscopy: 1.28 (3H, d), 3.61 (3H, s), 3.96-4.06 (1H, m), 6.91-6.97 (1H, m), 7.20 (2H, dd), 7.27 (2H, dd).

Referring to the method of Reference Example, the iii-2 was in place of the iii-0 to react with anhydrous entecavir, and the reaction product was separated by silica gel column chromatography to obtain the compound II-2 with a yield of 13%. $^1$H NMRδ (ppm, DMSO-$d_6$, 400 MHz): 1.24 (3H, d), 2.04-2.09 (1H, m), 2.26-2.33 (1H, m), 2.75 (1H, s, br), 3.61 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.20 (2H, dd), 7.23 (2H, dd), 7.66 (1H, s), 10.55 (1H, s).

Example 3: 2-amino-1,9-dihydro-9-[(1S,3R,4S)-4-hydroxy-3-((S)-((S)-1-methoxycarbonylethylamino-(4-chloro-phenyl)oxy-phosphoryl)-oxymethyl)-2-methylenecyclopentyl]-6H-purin-6-one (11-3)

II-3

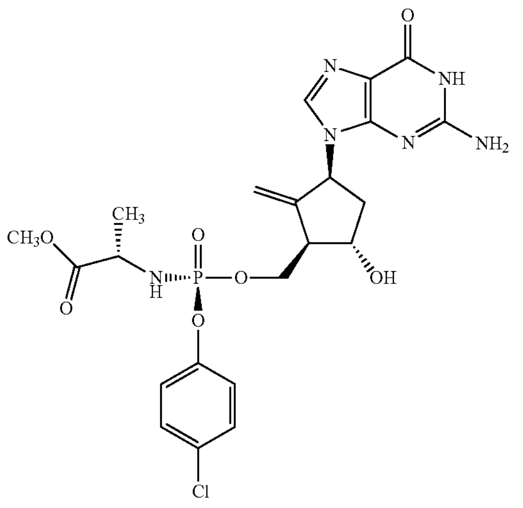

Referring to the method in step 1.1 of Example 1, dichlorophosphoric acid-(p-chloro-phenol)ester was in place of dichlorophosphoric acid phenol ester to react with L-alanine methyl ester hydrochloride and pentafluorophenol successively, thus obtaining methyl (S)-2-[-(S)-(2,3,4,5,6-pentafluoro-phenoxy)-(p-chlorophenoxy)-phosphoramide]-propionate (iii-3) with a yield of 36% and a de value of 98.3%. δ (ppm, DMSO-$d_6$, 400 MHz) in $^1$H NMR spectroscopy: 1.28 (3H, d), 3.61 (3H, s), 3.96-4.06 (1H, m), 6.91-6.97 (1H, m), 7.23 (2H, dd), 7.37 (2H, dd).

Referring to the method of Reference Example, the iii-3 was in place of the iii-0 to react with anhydrous entecavir, and the reaction product was separated by silica gel column chromatography to obtain the compound II-3 with a yield of 16%. $^1$H NMRδ (ppm, DMSO-$d_6$, 400 MHz): 1.24 (3H, d), 2.04-2.09 (1H, m), 2.26-2.33 (1H, m), 2.75 (1H, s, br), 3.61 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.23 (2H, dd), 7.42 (2H, dd), 7.66 (1H, s), 10.55 (1H, s).

Example 4: 2-amino-1,9-dihydro-9-[(1S,3R,4S)-4-hydroxy-3-((S)-((S)-1-methoxycarbonylethylamino-(4-bromo-phenyl)oxy-phosphoryl)-oxymethyl)-2-methylenecyclopentyl]-6H-purin-6-one (11-4)

II-4

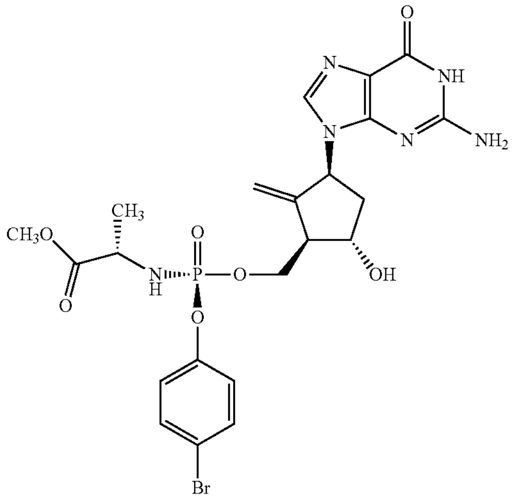

Referring to the method in step 1.1 of Example 1, dichlorophosphoric acid-(p-bromo-phenol)ester was in place of dichlorophosphoric acid phenol ester to react with L-alanine methyl ester hydrochloride and pentafluorophenol successively, thus obtaining methyl (S)-2-[-(S)-(2,3,4,5,6-pentafluoro-phenoxy)-(p-bromophenoxy)-phosphoramide]-propionate (iii-4) with a yield of 41% and a de value of 98.0%. δ (ppm, DMSO-$d_6$, 400 MHz) in $^1$H NMR spectroscopy: 1.28 (3H, d), 3.61 (3H, s), 3.96-4.06 (1H, m), 6.91-6.97 (1H, m), 7.23 (2H, dd), 7.41 (2H, dd).

Referring to the method of Reference Example, the iii-4 was in place of the iii-0 to react with anhydrous entecavir, and the reaction product was separated by silica gel column chromatography to obtain the compound II-4 with a yield of 21%. δ (ppm, DMSO-$d_6$, 400 MHz) in $^1$H NMR spectroscopy: 1.24 (3H, d), 2.04-2.09 (1H, m), 2.26-2.33 (1H, m), 2.75 (1H, s, br), 3.61 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.21 (2H, dd), 7.48 (2H, dd), 7.66 (1H, s), 10.55 (1H, s).

Example 5: 2-amino-1,9-dihydro-9-[(1S,3R,4S)-4-hydroxy-3-((S)-((S)-1-methoxycarbonylethylamino-(4-methoxy-phenyl)oxy-phosphoryl)-oxymethyl)-2-methylenecyclopentyl]-6H-purin-6-one (II-5)

II-5

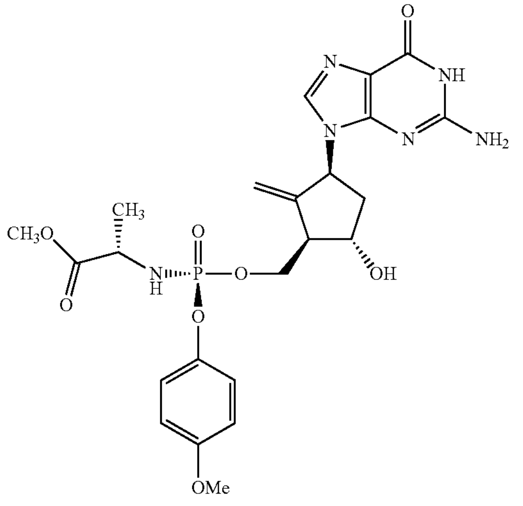

Referring to the method in step 1.1 of Example 1, dichlorophosphoric acid-(p-methoxy-phenol)ester was in place of dichlorophosphoric acid phenol ester to react with L-alanine methyl ester hydrochloride and pentafluorophenol successively, thus obtaining methyl (S)-2-[-(S)-(2,3,4,5,6-pentafluoro-phenoxy)-(p-methoxy-phenoxy)-phosphoramide]-propionate (iii-5) with a yield of 31% and a de value of 98.2%. δ (ppm, DMSO-$d_6$, 400 MHz) in $^1$H NMR spectroscopy: 1.28 (3H, d), 3.61 (3H, s), 3.96-4.06 (1H, m), 6.91-6.97 (1H, m), 7.13 (2H, dd), 7.17 (2H, dd).

Referring to the method of Reference Example, the iii-5 was in place of the iii-0 to react with anhydrous entecavir, and the reaction product was separated by silica gel column chromatography to obtain the compound II-5 with a yield of 12%. δ (ppm, DMSO-$d_6$, 400 MHz) in $^1$H NMR spectroscopy: 1.24 (3H, d), 2.04-2.09 (1H, m), 2.26-2.33 (1H, m), 2.75 (1H, s, br), 3.61 (3H, s), 3.70 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.10 (2H, dd), 7.12 (2H, dd), 7.66 (1H, s), 10.55 (1H, s).

Example 6: 2-amino-1,9-dihydro-9-[(1S,3R,4S)-4-hydroxy-3-((S)-((S)-1-methoxycarbonylethylamino-(4-methyl-phenyl)oxy-phosphoryl)-oxymethyl)-2-methylenecyclopentyl]-6H-purin-6-one (II-6)

II-6

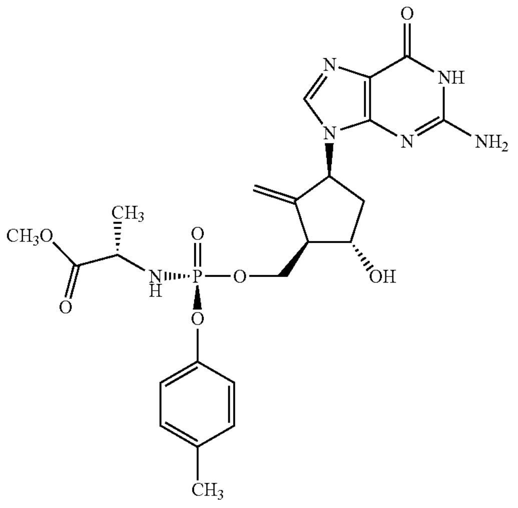

Referring to the method in step 1.1 of Example 1, dichlorophosphoric acid-(p-methyl-phenol)ester was in place of dichlorophosphoric acid phenol ester to react with L-alanine methyl ester hydrochloride and pentafluorophenol successively, thus obtaining methyl (S)-2-[-(S)-(2,3,4,5,6-pentafluoro-phenoxy)-(p-methylphenoxy)-phosphoramide]-propionate (iii-6) with a yield of 38% and a de value of 98.7%. δ (ppm, DMSO-$d_6$, 400 MHz) in $^1$H NMR spectroscopy: 1.28 (3H, d), 2.28 (3H, s), 3.61 (3H, s), 3.96-4.06 (1H, m), 6.91-6.97 (1H, m), 7.12 (2H, dd), 7.20 (2H, dd).

Referring to the method of Reference Example, the iii-6 was in place of the iii-0 to react with anhydrous entecavir, and the reaction product was separated by silica gel column chromatography to obtain the compound II-6 with a yield of 19%). δ (ppm, DMSO-$d_6$, 400 MHz) in $^1$H NMR spectroscopy: 1.24 (3H, d), 2.04-2.09 (1H, m), 2.26-2.31 (4H, m), 2.75 (1H, s, br), 3.61 (3H, s), 3.85-3.91 (1H, m), 4.07-4.11 (1H, m), 4.21-4.27 (2H, m), 4.61 (1H, s, br), 5.03 (1H, d), 5.16 (1H, s, br), 5.36 (1H, m), 6.01-6.07 (1H, m), 6.39 (2H, s, br), 7.06-7.21 (4H, m), 7.36-7.40 (2H, m), 7.66 (1H, s), 10.55 (1H, s).

Example 7: Evaluation of Metabolic Stability in Human Plasma and Human Liver Microsome

Example 7.1: Evaluation of Stability in Human Plasma

To 1 mL of human plasma containing 5 mM $MgCl_2$ was added 2 μL of a solution of 50 mM compound to be tested in DMSO, and the mixture was incubated at 37° C. 100 μL of sample was taken at different time points, into which 200 μL of methanol was added, and the mixture was centrifuged at 14000 rpm at 4° C. for 30 min. 100 μL of supernatant was taken, into which 100 μL of methanol was added, and the mixture was frozen at −20° C. for later use.

Example 7.2: Evaluation of Metabolic Stability in Human Liver Microsome

To 1 mL of buffer containing 5 mM $MgCl_2$ and 50 mM $K_2HPO_4$ (pH 7.4) was added 2 μL of a solution of 50 mM compound to be tested in DMSO, then human liver S9 components were added to reach 4 mg/mL, and the mixture was incubated at 37° C. 100 μL of sample was taken at different time points, into which 300 μL of methanol was added, and the mixture was centrifuged at 14000 rpm for 30 min at 4° C. 100 μL of supernatant was taken, into which 100 μL of methanol was added, and the mixture was frozen at −20° C. for later use.

The content of the compound to be tested in plasma or liver microsome was determined by LC-MS/MS, and the half-life was calculated. Instruments: Prominence 20 A liquid chromatograph from Shimadzu, API 4000 Q-TRAP mass spectrometer from Applied Biosystems; mass spectrometry conditions: ESI negative ion detection; chromatographic column: Diamonsil $C_{18}$ (100×4.6 mm, 5 μm) chromatographic column; column temperature: 40° C.; flow rate: 0.5 mL/min. Mobile phase A: methanol; mobile phase B: 5% aqueous methanol solution (containing 2 mM ammonium formate); flow rate: 0.5 mL/min; gradient elution as shown in the following table:

| Time (min) | 0 | 3 | 3.5 | 5.5 | 5.6 | 8 |
|---|---|---|---|---|---|---|
| A(%) | 20 | 60 | 95 | 95 | 20 | 20 |
| B(%) | 80 | 40 | 5 | 5 | 80 | 80 |

The results are shown in Table 1:

TABLE 1

Stability in human plasma and liver microsome

| The tested compound | $T_{1/2}$ (h) Plasma (h) | $T_{1/2}$ (h) Liver microsome |
|---|---|---|
| I-5-B | >24 | 0.40 |
| II-1 | 15.3 | 0.27 |
| II-2 | 10.6 | 0.13 |
| II-3 | 7.5 | 0.06 |
| II-4 | 6.2 | 0.06 |
| II-5 | 4.9 | 0.03 |
| II-6 | 10.8 | 0.19 |

The above results show that the stability of the target compound in both plasma and liver microsome is lower than that of the I-5-B; and similar to the I-5-B, the stability of the target compound is significantly higher in plasma than in liver microsome. This suggests that the target compound has a higher metabolic transformation rate than the I-5-B, while they have similar liver targeting property.

Example 8: Pharmacokinetic Evaluation in Rats

SD rats (weighing 180 to 220 g, 6 rats each group, half male and half female) were fasted for 12 h before administration. The compound to be tested was added into 0.5% sodium carboxymethylcellulose solution, mixed homogenously and administered intragastrically (the administration dose was 100 μmol/kg). Before administration and 0.25 h, 0.5 h, 1 h, 2 h, 3 h, 4 h, 5 h, 6 h, 8 h, 10 h, 12 h and 24 h after administration, 0.3 mL of blood was collected from the jugular vein separately, anticoagulated with sodium heparin, centrifuged to separate out the plasma, which was stored at −80° C. for determination.

50 μL of drug-containing plasma was taken, 50 μL of methanol and 100 μL of internal-standard acetaminophen methanol solution were added, and the mixture was vortexed for 1 min and centrifuged at 12000 rpm for 10 min at 4° C. The supernatant was taken and placed in an internal insert tube for quantitative analysis by LC-MS/MS (the method was the same as that in Example 7). The pharmacokinetic parameters of entecavir in blood were calculated by applying WinNonlin 6.3 pharmacokinetic software and selecting a non-compartmental model statistical moment method. The results are shown in Table 2:

TABLE 2

Results of pharmacokinetic evaluation in rats

| Pharmacokinetic parameters | I-5-B | II-1 | II-2 | II-5 | II-6 |
|---|---|---|---|---|---|
| $C_{max}$(nM) | 4723 ± 1437 | 6394 ± 1885 | 4380 ± 865 | 1239 ± 410 | 9423 ± 1964 |
| $T_{max}$( h) | 3.75 ± 0.500 | 2.60 ± 0.548 | 2.67 ± 0.816 | 1.17 ± 0.683 | 3.50 ± 0.577 |
| $AUC_{0\text{-}t}$(h*nM) | 31549 ± 11706 | 36050 ± 12689 | 27661 ± 7669 | 6313 ± 2299 | 40610 ± 12899 |
| $AUC_{0\text{-}\infty}$(h*nM) | 31902 ± 11863 | 38088 ± 13834 | 28533 ± 8347 | 6462 ± 2391 | 41382 ± 13229 |
| $MRT_{0\text{-}t}$(h) | 5.25 ± 0.720 | 5.11 ± 0.355 | 5.73 ± 0.741 | 4.37 ± 0.726 | 5.12 ± 0.533 |
| $MRT_{0\text{-}\infty}$(h) | 5.52 ± 0.731 | 5.86 ± 0.775 | 6.46 ± 1.00 | 4.93 ± 0.740 | 5.57 ± 0.974 |
| $V_d$(L/kg) | 20.0 ± 10.2 | 18.1 ± 11.3 | 25.8 ± 9.95 | 23.5 ± 9.08 | 14.4 ± 4.00 |
| CL(L/h/k g) | 3.36 ± 1.46 | 2.88 ± 1.44 | 3.53 ± 0.943 | 3.29 ± 1.18 | 2.49 ± 0.912 |
| $t_{1/2}$(h) | 4.05 ± 0.287 | 4.22 ± 0.933 | 5.11 ± 1.46 | 5.04 ± 0.967 | 4.17 ± 1.04 |

The above results show that after compounds II-1 and II-6 were intragastrically administered to rats, the bioavailability of entecavir was significantly higher than that of the I-5-B.

Example 9: Pharmacokinetic Evaluation in Beagle Dogs

Male beagle dogs (7-8 months old, weighing 7-10 kg) were randomly divided into groups (2 beagle dogs per group) and weighed. The beagle dogs were fasted for 12 h before administration. The sample to be tested at a certain concentration was ground and suspended in 0.5% sodium carboxymethylcellulose solution, and II-1 (5 mg/kg), II-6 (5.13 mg/kg) or I-5-B (5.27 mg/kg) was administered intragastrically to the beagle dogs. Before administration and 0.5 h, 1 h, 2 h, 4 h, 6 h, 8 h, 10 h and 24 h after administration, 0.5 mL of blood was collected from the cephalic vein of forelimb separately, anticoagulated with sodium heparin, centrifuged to separate out the plasma, which was stored at −80° C. for determination.

50 μL of drug-containing plasma was taken, into which 50 μL of methanol and 100 μL of internal-standard acetaminophen methanol solution were added, and the mixture was vortexed for 1 min and centrifuged at 12000 rpm for 10 min at 4° C. The supernatant was taken and placed in an internal insert tube for quantitative analysis by LC-MS/MS (the method was the same as that in Example 7). The pharmacokinetic parameters of entecavir or prodrug prototype in blood after administration of the target compound were calculated by applying WinNonlin 6.3 pharmacokinetic software and selecting a non-compartmental model statistical moment method. The maximum plasma concentrations are shown in Table 3:

TABLE 3

Maximum plasma concentrations of prodrug prototype and entecavir

| Compounds | Cmax(ng/ml) Prodrug prototype | Cmax(ng/ml) Entecavir | Cmax (entecavir)/ Cmax (prodrug) |
|---|---|---|---|
| I-5-B | 863.53 | 1425.96 | 1.65 |
| II-1 | 331.42 | 2358.11 | 7.12 |
| II-6 | 632.60 | 781.45 | 1.24 |

The results show that after the compound II-1 was administered intragastrically to beagle dogs, the plasma concentration of the prodrug prototype was significantly lower than that of the I-5-B, while the plasma concentration of the entecavir was significantly higher than that of the I-5-B, which indicates that the metabolic transformation of the II-1 is more complete after administration.

Example 10: Evaluation of Tissue Distribution in Beagle Dogs

Male beagle dogs (7-8 months old, weighing 7-10 kg) were randomly divided into groups (4 beagle dogs per group) and weighed. The sample to be tested at a certain concentration was ground and suspended in 0.5% sodium carboxymethylcellulose solution, and the sodium carboxymethylcellulose suspension of the II-1 (dose: 5 mg/kg) or the I-5-B (dose: 5.27 mg/kg) was administered intragastrically once daily for 4 consecutive days. After the last administration, the beagle dogs were fasted for 4 h but had free access to water. The animals were anesthetized with pentobarbital, and the viscera were taken, rinsed with ice brine and frozen in liquid nitrogen for later use.

The frozen tissue was taken, frozen 70% methanol (containing 20 mM EDTA/EGTA) 3 times the frozen tissue in amount was added, and homogenate was prepared and centrifuged at 12000 rpm for 10 min at 4° C. The supernatant was taken and placed in an internal insert tube for quantitative analysis by LC-MS/MS to determine the content of entecavir triphosphate in each tissue. Instrument: TSQ Quantum liquid chromatography-mass spectrometer (LC/MS/MS) from Finnigan, USA, consisting of a Finnigan Surveyor LC pump, a Surveyor AS autosampler, an Electrospray ionization (ESI) and a triple tandem mass spectrometer. The control software was Xcalibur 1.4, and a Lcquan 2.0 data processing system was adopted for mass spectrum data analysis. The chromatographic column was a Discovery ODS column (250 mm×4.6 mm, 5 m) and a C18 guard column (4 mm×3.0 mm); the mobile phase was methanol-water-formic acid (10-30:90-70:0.5, V/V/V); the flow rate was 0.7 mL/min; the injection volume was 20 μL; the column temperature was room temperature.

The results are shown in Table 4:

TABLE 4

Content of entecavir triphosphate in viscera (ng/g)

| Compounds | Liver | Lung | Thymus gland | Lymph node | Spleen |
|---|---|---|---|---|---|
| I-5-B | 2079.6 | 672.5 | 709.2 | 1277.0 | 641.9 |
| II-1 | 3558.5 | 392.2 | 810.7 | 1175.3 | 559.7 |

The results show that after the compound II-1 was intragastrically administered to beagle dogs, the content of the active entecavir triphosphate in the liver is significantly higher than that of the I-5-B, and this suggests that the compound II-1 has better liver targeting property.

The embodiments of the present disclosure have been described above. However, the present disclosure is not limited thereto. Any modification, equivalent, improvement and the like made without departing from the spirit and principle of the present disclosure shall fall within the protection scope of the present disclosure.

The invention claimed is:

1. A compound of formula II:

II

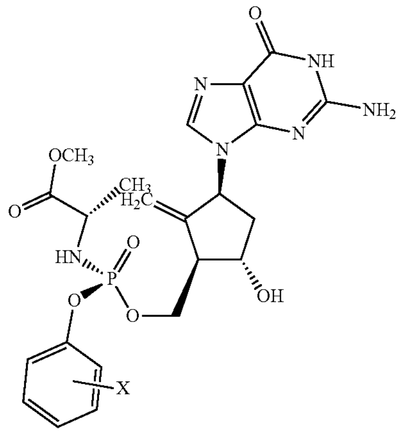

or a non-toxic pharmaceutically acceptable salt thereof, wherein:

X is H, halogen, R, or OR; and

R is a $C_{1-3}$ alkyl, wherein the $C_{1-3}$ alkyl is optionally substituted with one or more substituents independently selected from the group consisting of halogen and OH.

2. The compound as claimed in claim 1, or a non-toxic pharmaceutically acceptable salt thereof, wherein R is a $C_{1-3}$ alkyl, wherein the $C_{1-3}$ alkyl is substituted with one halogen substituent or one OH substituent.

3. The compound as claimed in claim 1, or a non-toxic pharmaceutically acceptable salt thereof, wherein R is $CH_3$, $CH_2CH_3$, or $CH_2CH_2CH_3$.

4. The compound as claimed in claim 1, or a non-toxic pharmaceutically acceptable salt thereof, wherein

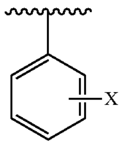

is:

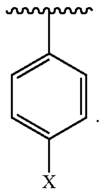

5. The compound as claimed in claim 1, or a non-toxic pharmaceutically acceptable salt thereof, wherein X is H, F, Cl, Br, $CH_3$, or $OCH_3$.

6. The compound as claimed in claim 1, or a non-toxic pharmaceutically acceptable salt thereof, wherein:

X is F, Cl, Br, or I; and

R is a $C_{1-3}$ alkyl, wherein the $C_{1-3}$ alkyl is optionally substituted with one or more substituents independently selected from the group consisting of F, Cl, Br, and OH.

7. The compound as claimed in claim 1, wherein the compound is selected from the group consisting of:

II-1

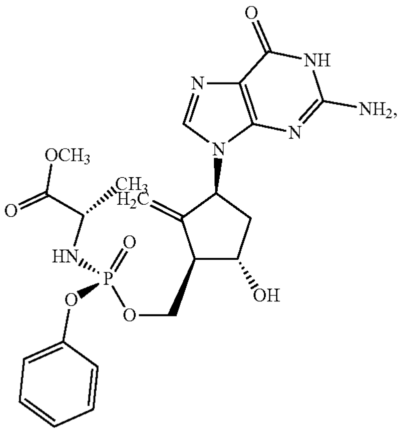

II-2

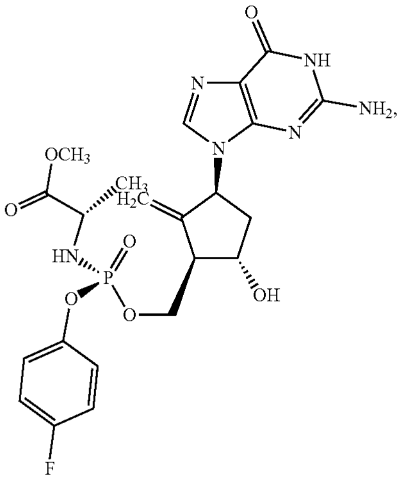

II-3

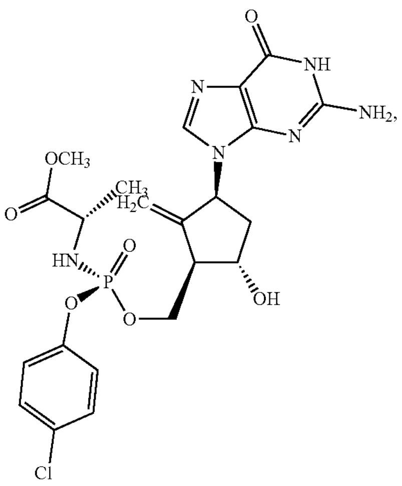

-continued

II-4

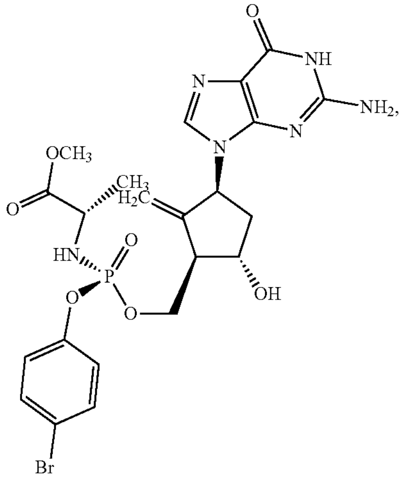

II-5

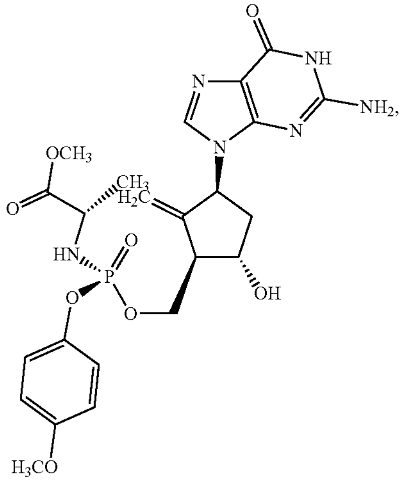

-continued

II-6

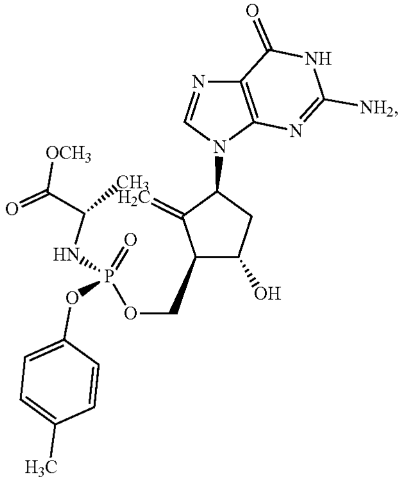

or a non-toxic pharmaceutically acceptable salt thereof.

8. A pharmaceutical composition comprising a pharmaceutically acceptable carrier and the compound as claimed in claim 1, or a non-toxic pharmaceutically acceptable salt thereof, as an active ingredient.

9. The pharmaceutical composition as claimed in claim 8, wherein the pharmaceutical composition is formulated as a capsule, a granule, a lozenge, a powder, a solution, a suspension, or a tablet.

10. A method for treating a hepatitis B virus infection in a subject, wherein the method comprises administering to the subject in need thereof a therapeutically effective amount of a medicament comprising the compound as claimed in claim 1, or a non-toxic pharmaceutically acceptable salt thereof.

11. A method for treating a hepatitis B virus infection in a subject, wherein the method comprises administering to the subject in need thereof a therapeutically effective amount of the pharmaceutical composition as claimed in claim 8.

* * * * *